United States Patent

Niedenbrueck et al.

Patent Number: 5,505,743
Date of Patent: Apr. 9, 1996

[54] VAT DYES

[75] Inventors: Matthias Niedenbrueck, Limburgerhof; Manfred Patsch, Wachenheim; Michael Schmitt, Worms, all of Germany

[73] Assignee: BASF Aktiengesellschaft, Ludwigshafen, Germany

[21] Appl. No.: 327,417

[22] Filed: Oct. 21, 1994

[30] Foreign Application Priority Data

Oct. 21, 1993 [DE] Germany .......... 43 35 974.4

[51] Int. Cl.⁶ .......... C09B 67/28; C07D 487/00
[52] U.S. Cl. .......... 8/650; 546/27; 548/417; 8/921; 8/918
[58] Field of Search .......... 546/27; 548/417; 8/650–653

[56] References Cited

U.S. PATENT DOCUMENTS

| | | | |
|---|---|---|---|
| 1,856,203 | 5/1932 | Wolff | 548/417 X |
| 2,232,700 | 2/1941 | Fleysher | 548/417 X |
| 2,677,693 | 5/1954 | Nawiasky et al. | 552/281 |
| 4,547,575 | 10/1985 | Tzikas | 546/27 |

FOREIGN PATENT DOCUMENTS

| | | |
|---|---|---|
| 88048 | 9/1983 | European Pat. Off. . |
| 307328 | 4/1929 | United Kingdom . |
| 703294 | 2/1954 | United Kingdom . |

*Primary Examiner*—Margaret Einsmann
*Attorney, Agent, or Firm*—Oblon, Spivak, McClelland, Maier & Neustadt

[57] ABSTRACT

Vat dyes obtainable by a) halogenation of dibenzanthrone with bromine in the presence of chlorosulfonic acid and of a halogenation catalyst to a bromine content from 26 to 32% by weight and a chlorine content from 1 to 5% by weight, and b) condensation of the isolated halogenation product with 1-aminoanthraquinone in a molar ratio from 1:2 to 1:2.5 in the presence of an inert solvent, the concentration of halogenated dibenzanthrone and 1-aminoanthraquinone together being at least 200 g/l of solvent are useful for dyeing or printing cellulose-containing textile material.

7 Claims, No Drawings

VAT DYES

The present invention relates to novel vat dyes obtainable by
a) halogenation of dibenzanthrone with bromine in the presence of chlorosulfonic acid and of a halogenation catalyst to a bromine content from 26 to 32% by weight and a chlorine content from 1 to 5% by weight, and
b) condensation of the isolated halogenation product with 1-aminoanthraquinone in a molar ratio from 1.2 to 1:2.5 in the presence of an inert solvent, the concentration of halogenated dibenzanthrone and 1-aminoanthraquinone together being at least 200 g/l of solvent.

The invention further relates to the preparation and use of these vat dyes.

Dyes which are to be used for dyeing textile material must have high fastness properties such as wash fastness and light fastness as well as color strength.

Cellulose-containing textile material is frequently dyed using vat dyes. These are frequently condensation products based on dibenzanthrone (violanthrone) and anthraquinones, in particular 1-aminoanthraquinone.

GB-A-703 294, U.S. Pat. No. 2,677,693, and GB-A-307 328 disclose the bromination of dibenzanthrone in the presence of chlorosulfonic acid and of sulfur, iodine or an aluminum halide as halogenation catalyst and the subsequent condensation of the bromination product with 1-aminoanthraquinone in nitrobenzene with reactant concentrations of 126 and 108 g/l of nitrobenzene, respectively.

However, the methods of preparation described therein lead only to incomplete conversion of the brominated dibenzanthrone and thus to a contamination of the vat dye by unconverted starting materials and also unhalogenated dibenzanthrone, which is why dyeings in the desired neutral gray shade cannot be achieved.

EP-A-88 048 describes vat dyes obtained by condensation of 1-aminoanthraquinone with excess brominated dibenzanthrone. In this case the bromination is carried out in the presence of sulfuric acid and iodine as halogen transfer agent.

But, again, the vat dyes thus prepared are not fully satisfactory; especially the fastness properties, including the wash fastness properties of light-colored dyeings, are in need of improvement.

It is an object of the present invention to provide novel vat dyes with which cellulose fibers can be dyed with high color strength and good fastness properties in neutral gray shades.

We have found that this object is achieved by the vat dyes defined at the beginning.

The invention also provides the thereby defined process for preparing these vat dyes.

The invention further provides the use of these vat dyes for dyeing or printing cellulose-containing textile material.

The novel vat dyes are advantageously obtainable by the process of the invention in which, in the first process step, dibenzanthrone is brominated in chlorosulfonic acid to a certain bromine content and the isolated product is then condensed in the second process step with 1-aminoanthraquinone in a certain molar ratio.

A bromination in chlorosulfonic acid gives products which have a different isomer distribution than the products of a bromination in sulfuric acid. In addition, the dibenzanthrones thus brominated also contain certain amounts of chlorine; that is, the bromination is accompanied by a simultaneous chlorination. Reaction of these halogenated products with 1-aminoanthraquinone results in condensation products which likewise have a different constitution than the products prepared starting from dibenzanthrone brominated in sulfuric acid. Regardless of whether or not the condensation products still contain residual halogen, especially chlorine, they constitute vat dyes of high color strength which represent an advance in the art and with which neutral gray dyeings having excellent fastness properties, even in light shades, can be obtained.

Generally the halogenation of the dibenzanthrone is carried on to a bromine content from 26 to 32, preferably from 28 to 30, % by weight to a chlorine content from 1 to 5, preferably from 3.5 to 5, % by weight.

The reaction medium used is chlorosulfonic acid, to which some aqueous sulfuric acid is preferably added in order that any free sulfur trioxide present may be trapped.

Advantageously the bromination is carried out in the presence of a halogenation catalyst. Of particular suitability are iodine and especially sulfur. Customary amounts are from 5 to 8% by weight, based on dibenzanthrone.

The reaction temperature depends on the desired degree of halogenation; it is preferably from 45° to 90° C.

In process terms, step a) will usually be carried out by initially charging the chlorosulfonic acid, then adding at from about 15° to 20° C., with stirring, initially the dibenzanthrone and then the halogenation catalyst, and subsequently introducing the bromine dropwise at room temperature. On completion of the addition of the bromine the mixture is generally heated over from about 5 to 8 h to the desired temperature and then generally stirred at that temperature for from about 10 to 15 h.

After the bromination has ended, the product can be isolated in a conventional manner, for example by pouring the reaction solution into ice-water, filtering off the resulting precipitate, and washing it neutral.

That the bromination in chlorosulfonic acid gives different products than the bromination in sulfuric acid is also evident from the fact that the condensation with 1-aminoanthraquinone is distinctly more difficult to carry out in the former case. This is the reason why existing processes only lead to unsatisfactory, incompletely converted condensation products.

This problem has been solved in the process of the invention by stipulating that the concentration of the starting materials—halogenated benzanthrone and 1-aminoanthraquinone—shall together be at least 200 g/l of solvent. There is basically no upper limit for the concentration, but the reaction mixture should still be stirrable, since only that will ensure complete conversion of the reactants.

Generally the 1-aminoanthraquinone and the halogenated dibenzanthrone are used in a molar ratio from 2.0:1 to 2.5:1, preferably from 2.2:1 to 2.4:1, particularly preferably from 2.2:1 to 2.3:1.

Suitable inert solvents for the condensation reaction include for example aromatics such as nitrobenzene and nitrotoluene, alkyl benzoates, in particular $C_1$-$C_6$-alkyl benzoates such as methyl benzoate, ethyl benzoate, propyl benzoate and butyl benzoate, and aliphatic carboxamides such as dimethylformamide, diethylformamide, dibutylformamide, dimethylacetamide, diethylacetamide and dibutylacetamide. Examples of particularly preferred solvents are nitrobenzene and methyl benzoate.

Advantageously the condensation is carried out in the presence of a customary acid-binding agent such as sodium hydroxide, sodium acetate, sodium carbonate, potassium hydroxide, potassium acetate or potassium carbonate, in particular sodium carbonate, and of a condensation aid based on copper, eg. elemental copper (as powder) and/or copper compounds such as copper oxide, copper acetate and copper(I) chloride. The acid-binding agent will usually be used in amounts from 1.1 to 1.3 mol equivalents, based on the aminoanthraquinone, while the amount of condensation aid will generally be from 0.4 to 0.8 mol equivalents, based on the halogen content of the halogenated dibenzanthrone.

The reaction temperature depends on the reflux temperature of the solvent used. Especially in the case of relatively low boiling solvents is it advisable to carry out the reaction in a closed system under its autogenous pressure.

The preferred procedure is to charge the solvent, the halogenated dibenzanthrone, the 1-aminoanthraquinone and the acid-binding agent initially and to remove as much water as possible from the initial charge, by refluxing, before the copper catalyst is added. The condensation reaction itself will generally have ended after from 10 to 15 h.

The vat dye formed can then be isolated and purified in a conventional manner by removing the solvent by steam distillation and subjecting the dye to decoppering, for example by refluxing with hydrochloric acid, collection on a filter, washing neutral and drying.

The process of the invention is an advantageous way of preparing the novel vat dyes. Owing to their good application properties, they are highly suitable for dyeing and printing cellulose-containing textile material.

EXAMPLES

Preparation and use of vat dyes according to the invention

A) Preparation a) Halogenation of dibenzanthrone

Halogenation product I

To a mixture of 2400 g of chlorosulfonic acid and 100 g of 75% strength by weight sulfuric acid were added at 15°–20° C. 600 g of dibenzanthrone. After subsequent stirring for one hour and addition of 40 g of sulfur, 300 g of bromine were added dropwise at room temperature over 30 min. The reaction mixture was then heated over 7 h to 80° C., stirred at 75°–80° C. for 14 h and subsequently poured onto ice-water. The product was filtered off, washed neutral and dried.

This yielded 868 g of halogenated dibenzanthrone having a bromine content of 29.8% by weight and a chlorine content of 4.1% by weight.

Halogenation product II

The preparation of I was repeated using only 270 g of bromine, heating the reaction mixture over 2 h to 50°–53° C. and stirring it at that temperature for 14.5 h.

This yielded 858 g of halogenated dibenzanthrone having a bromine content of 26.9% by weight and a chlorine content of 1.2% by weight.

Halogenation product III

The preparation of I was repeated using 247 g of bromine, heating the reaction mixture over 6 h to 50°–55° C. and stirring it at that temperature for 14 h.

This yielded 847 g of halogenated dibenzanthrone having a bromine content of 26.1% by weight and a chlorine content of 1.2% by weight.

b) Condensation of the halogenated dibenzanthrone with 1-aminoanthraquinone

A mixture of 600 ml of the solvent S, x g (mol, based on the dibenzanthrone structure) of halogenation product of a), y g (mol) of 1-aminoanthraquinone (AA) and a g of sodium carbonate (anhydrous soda) was dewatered by refluxing (nitrobenzene: about 212° C., methyl benzoate: about 202° C.) for one hour. After addition of b g of copper catalyst the mixture was stirred at the reflux temperature for 10 h (15 h in Example 7).

The solvent was then substantially removed by steam distillation.

The vat dye was filtered off, decoppered by refluxing with 750 ml of 5% strength by weight hydrochloric acid for 5 h (Examples 6 and 7: 10% strength by weight hydrochloric acid, 3 h), filtered off again, washed neutral and dried.

Details of these experiments and the results thereof are listed below in the table.

B) Use

The vat dyes obtained were used to dye a cotton fabric sample as follows:

50 mg (gray dyeing) or 800 mg (black dyeing) of the respective dye were vatted at 25° C. in 200 ml of an aqueous solution containing 6.6 ml of sodium hydroxide solution 38° Bé and and 1.5 g of sodium dithionite in the course of 10 min.

This vat was entered with 10 g of cotton fabric. It was then heated over 30 min to initially 60° C. and then over 15 min to 80° C. Thereafter dyeing was continued at that temperature for 30 min.

After the cotton had been squeezed off, it was air-oxidized, and the dyeing was finished in a conventional manner.

All cases gave neutral gray or black dyeings having excellent fastness properties.

TABLE

| Ex. | Solvent | x g (mol) of halogenation product | y g (mol) of AA | a g of soda | b g of Cu cat. | Yield [g] | Content [% by wt.] bromine | Content [% by wt.] chlorine | Dyeing on cotton |
|---|---|---|---|---|---|---|---|---|---|
| 1 | S1* | 71.4 (0.10) I | 49.1 (0.22) | 35 | 13.5 CuCl | 101.0 | 1.8 | 0.7 | neutral gray or black |
| 2 | S1 | 69.1 (0.10) I | 50.9 (0.23) | 36 | 14.0 CuCl | 99.5 | 1.1 | 0.6 | neutral gray or black |
| 3 | S1 | 65.4 (0.10) I | 54.6 (0.24) | 35 | 13.5 CuCl | 100.0 | <0.5 | <0.5 | neutral gray or black |
| 4 | S2** | 70.3 (0.11) II | 49.1 (0.22) | 35 | 6.7 Cu + 6.7 CuCl | 104.4 | 1.8 | <0.5 | neutral gray or black |
| 5 | S1 | 66.8 (0.11) III | 53.5 (0.24) | 38 | 13.5 CuCl | 108.0 | 1.2 | <0.5 | neutral gray or black |
| 6 | S2 | 71.4 (0.10) I | 49.1 (0.22) | 35 | 6.7 Cu + 6.7 CuCl | 100.7 | 1.8 | 0.7 | neutral gray or black |

TABLE-continued

| Ex. | Solvent | x g (mol) of halogenation product | y g (mol) of AA | a g of soda | b g of Cu cat. | Yield [g] | Content [% by wt.] bromine | chlorine | Dyeing on cotton |
|---|---|---|---|---|---|---|---|---|---|
| 7 | S2 | 66.8 (0.11) III | 53.5 (0.24) | 38 | 8.7 Cu | 80.6 | 1.8 | <0.2 | neutral gray or black |

*S1 ≐ nitrobenzene
**S2 ≐ methyl benzoate

We claim:

1. A vat dye prepared by a process comprising:
   (a) halogenating dibenzanthrone with bromine in the presence of chlorosulfonic acid and a halogenation catalyst to a bromine content of from 26 to 32% by weight and a chlorine content of from 1 to 5% by weight and
   (b) condensing the isolated halogenation product with 1aminoanthraquinone in a molar ratio of from 1:2 to 1:2.5 in the presence of an inert solvent, the concentration of the halogenated dibenzanthrone and 1-aminoanthraquinone together being at least 200 g/l of solvent.

2. The vat dye as claimed in claim 1, wherein the halogenation of step (A) results in a bromine content ranging from 28 to 30% by weight and a chlorine content ranging from 3.5 to 5% by weight in the dibenzanthrone.

3. The vat dye of claim 1, wherein the molar ratio of said halogenation product of step (A) to 1-aminoanthraquinone ranges from 1:2.2 to 1:2.3.

4. A method for dyeing or printing cellulose-containing textile material, which comprises:
   dyeing a cellulose-containing textile material with the vat dye of claim 6.

5. A process for preparing vat dyes, which comprises:
   (a) halogenating dibenzanthrone with bromine in the presence of chlorosulfonic acid and a halogenation catalyst to a bromine content of from 26 to 32% by weight and a chlorine content of from 1 to 5% by weight and
   (b) condensing the isolated halogenation product with 1aminoanthraquinone in a molar ratio of from 1:2 to 1:2.5 in the presence of an inert solvent, the concentration of the halogenated dibenzanthrone and 1-aminoanthraquinone together being at least 200 g/l of solvent.

6. The process of claim 5, wherein the reaction temperature of step (A) ranges from 45° to 90° C.

7. The process of claim 5, wherein the halogenation of step (A) is conducted for a time ranging from about 10 to 15 hours.

* * * * *